United States Patent [19]
Williams et al.

[11] Patent Number: 5,663,054
[45] Date of Patent: Sep. 2, 1997

[54] DETERMINATION OF STEROIDS BY COMPETITIVE IMMUNOASSAY

[75] Inventors: Gregg T. Williams, Villa Park; William R. Groskopf; Harold N. Baker, both of Libertyville; Dalmacio A. Agdeppa, Morton Grove, all of Ill.

[73] Assignee: Abbott Laboratories, Abbott Park, Ill.

[21] Appl. No.: 398,226

[22] Filed: Mar. 3, 1995

[51] Int. Cl.$^6$ .................. G01N 33/53; G01N 33/542; G01N 33/537; G01N 33/543
[52] U.S. Cl. .................. 435/7.93; 435/7.9; 435/7.92; 435/806; 436/501; 436/510; 436/523; 436/524; 436/906
[58] Field of Search .................. 436/501, 510, 436/906, 523–524; 435/806, 7.9, 7.92, 7.93

[56] References Cited

U.S. PATENT DOCUMENTS

| | | | |
|---|---|---|---|
| 4,275,149 | 6/1981 | Litman et al. | |
| 4,282,325 | 8/1981 | Rubenstein et al. | 435/188 |
| 4,857,652 | 8/1989 | Schaap. | |
| 4,962,192 | 10/1990 | Schaap. | |
| 4,990,443 | 2/1991 | Huber et al. | 435/7.9 |
| 5,342,760 | 8/1994 | Baker et al. | 435/7.92 |
| 5,386,017 | 1/1995 | Schaap. | |
| 5,395,938 | 3/1995 | Ramakrishnan | 546/104 |
| 5,491,071 | 2/1996 | Adamczyk et al. | 435/25 |

FOREIGN PATENT DOCUMENTS

| | | |
|---|---|---|
| 0200960 | 12/1986 | European Pat. Off. |
| 0383313 | 8/1990 | European Pat. Off. |
| 383313 | 8/1990 | European Pat. Off. |
| WO8800695 | 1/1988 | WIPO. |
| WO9325672 | 12/1993 | WIPO. |

OTHER PUBLICATIONS

M. Forest et al., O-(Carboxymethyl) Oxime Steroidal Haptens Linked in the C3 Position: Study of the Characteristics of Antibodies Against 17Alpha-Hydroxyprogesterone and Testosterone and of Their Evolution with Time, *Steroids: Structure, Function, and Regulation*, vol. 28, No. 6, pp. 815–827 (1976).

Database WPI, Section Ch, Week 8606, Derwent Publications Ltd., London, GB; XP002008417 & JP, A, 60 260 592 (Teikoku Hormone Mfg Ltd.), 23 Dec. 1985.

*Primary Examiner*—Toni R. Scheiner
*Assistant Examiner*—Sheela J. Huff
*Attorney, Agent, or Firm*—David L. Weinstein

[57] ABSTRACT

A method and kit for measurement of asteroid by means of a competitive immunoassay, preferably a competitive enzyme immunoassay. The method and kit involve the use of asteroid analogue conjugated to a label. The steroids that are amenable to detection by the method and kit of the present invention include estradiol and progesterone.

The method comprises the steps of:

a. incubating a mixture of a test sample suspected of containing a given steroid, a solid phase coupled to an antibody specific for that steroid, and a conjugate of an analogue of that steroid to form steroid/antibody complexes and conjugate/antibody complexes on said solid phase;

b. separating said solid phase from said mixture;

c. measuring the amount of label present in said mixture or in said solid phase; and d. determining the amount of steroid in said sample from the amount of label.

The kit comprises a solid phase coupled to an antibody specific for a steroid and a conjugate of an analogue of that steroid.

24 Claims, 6 Drawing Sheets

DETERMINATION OF STEROIDS BY COMPETITIVE IMMUNOASSAY

BACKGROUND OF THE INVENTION

1. Field of the Invention

This invention relates to detection and measurement of steroids in biological fluids, and, more particularly, detection and measurement of steroids by means of competitive immunoassay.

2. Discussion of the Art

Detection and measurement of steroids in biological fluids is important for a variety of reasons. For example, the amount of a particular steroid in a biological fluid can be used to assist in diagnosing the occurrence of an endocrinological disorder, to monitor the amount of hormone required in hormonal replacement therapy, or to assess fertility. Determination of the presence and amount of steroids in a biological fluid can be determined by competitive diagnostic assay. Small molecule, competitive diagnostic assays require a labeled component that can compete with the analyte for available antibody sites. Examples of the labeled component include radioactive tracers, fluorophore/hapten conjugates, and enzyme/hapten conjugates. Typically, the labeled component consists of the analyte or an analogue of the analyte coupled to a label. The labeled component is typically referred to as a conjugate.

Estradiol (1,3,5(10)-estratrien-3,17α-diol) is an analyte, the detection and measurement of which is of great importance in the area of fertility testing. Estradiol is secreted by the ovary and placenta. It is synthesized by the aromatization of androgens in the thecal and granulosa cells of the ovary and placenta. The aromatization is stimulated by follitropin (FSH). Estradiol synthesis in turn stimulates production of lutropin (LH) receptors necessary for the synthesis of androgen precursors.

Estradiol is important for female sexual differentiation during gestation, sexual development at the onset of puberty, and regulation of the menstrual cycle. The menstrual cycle is the result of a precise coordination of the functional characteristics of the central nervous system, the hypothalamus, the pituitary, the ovary, and the endometrium, which regulate the cyclic release of Gonadotropin Releasing Hormone (GnRH), LH and FSH, and ovarian steroids (estradiol and progesterone). Estradiol is involved in both the stimulation and inhibition of the release of the gonadotropins, exerting both a positive and a negative feedback. Early in the follicular phase, ovarian secretion of estradiol from the thecal and granulosa cells is modest. During the follicular phase, estradiol stimulates endometrial growth (repairing the endometrium after menses). Toward mid-cycle, LH production increases and results in the release of the ovum by the rupture of the developed follicle. After ovulation, estradiol secretion declines slightly. During the luteal phase, estradiol along with progesterone are secreted by the corpus luteum, stimulating further endometrial growth. If the ovum is not fertilized, there is a further drop in estradiol and progesterone. This drop in estradiol and progesterone initiates menses.

The measurement of estradiol is important for the evaluation of normal sexual development (menarche), causes of infertility (anovulation, amenorrhea, dysmenorrhea), and menopause. Normal estradiol levels are lowest at menses and during the early follicular phase (25–75 pg/mL). The levels rise in the late follicular phase to a peak of 200–600 pg/mL just before the LH surge initiates ovulation. As LH peaks, estradiol begins to decrease before rising again during the luteal phase (100–300 pg/mL). If conception does not take place, estradiol falls further to its lowest levels, thus initiating menses. If conception occurs, estradiol levels continue to rise, reaching levels of 1–5 ng/mL during the first trimester, 5–15 ng/mL during the second trimester, and 10–40 ng/mL during the third trimester. During menopause, estradiol levels remain low.

There are various methods for measuring estradiol levels in serum. However, many of these methods utilize radioactive elements as labels and suffer from several disadvantages. Several of these methods are described in U.S. Pat. No. 5,342,760 (column 1, line 54 through column 3, line 30) and are incorporated herein by reference. U.S. Pat. No. 5,342,760 discloses and claims a useful method for determination of estradiol by competitive immunoassay. However, the method claimed in this patent is only effective with a limited number of antibodies.

Progesterone (4-pregnen-3,20-dione) is an analyte, the detection and measurement of which is of great importance in the area of assessing the occurrence of ovulation, conception, the risk of abortion, or ectopic pregnancy.

In the mitochondria, cholesterol is first converted to pregnenolone via a cytochrome P-450 enzyme-dependent side chain cleavage followed by hydroxylation. Pregnenolone is then converted to progesterone in a reaction catalyzed by 3β-hydroxysteroid dehydrogenase and isomerase enzymes (3β-HSD). Progesterone is produced primarily by the corpus luteum of the ovary in normally menstruating women and to a lesser extent by the adrenal cortex. At approximately the sixth week of pregnancy, the placenta becomes the major producer of progesterone. In the circulation of blood, approximately 97–98% of the progesterone is bound to albumin or Cortisol Binding Protein. Progesterone is metabolized, primarily in the liver, to pregnanediol and its water soluble sulfate and glucuronide derivatives and excreted in the urine.

The major functions of progesterone are in the preparation of the uterus for implantation and maintaining pregnancy. During the follicular phase, progesterone levels remain low (0.2–1.5 ng/mL). Following the LH surge and ovulation, luteal cells in the ruptured follicle produce progesterone in response to LH. During the luteal phase, progesterone rises rapidly to a maximum of 10–20 ng/mL at the fifth to seventh day following ovulation. If pregnancy does not occur, progesterone levels decrease during the last four days of the menstrual cycle due to the regression of the corpus luteum.

If conception occurs, the levels of progesterone are maintained at mid-luteal levels by the corpus luteum until about the sixth week. At that time the placenta becomes the main source of progesterone and levels rise from approximately 10–50 ng/mL in the first trimester to 50–280 ng/mL in the third trimester.

Serum progesterone is a reliable indicator of either natural or induced ovulation because of its rapid rise following ovulation. Disorders of ovulation, including anovulation, are relatively frequent and are responsible for infertility in approximately 15 to 20% of patients. Progesterone levels are abnormally low in these patients during the mid-luteal phase.

Luteal phase deficiency is a reproductive disorder associated with infertility and spontaneous abortion. It is thought to occur in 10% of infertile women. It is believed that infertility and pregnancy wastage associated with this disorder are caused by inadequate maturation and development of the endometrium. The failure of the endometrium is thought to be attributable to insufficient progesterone production by the corpus luteum. Serum progesterone levels in the luteal phase are lower than normal in women with luteal phase deficiency.

Measurement of progesterone in the first ten weeks of gestation has been shown to be a reliable predictor and an effective tool for the diagnosis and treatment of patients with threatened abortion and ectopic pregnancy. Suppressed progesterone levels (10–15 ng/mL) in the presence of detectable amounts of human chroionic gonadotropin (hCG) is highly suggestive of threatened abortion or ectopic pregnancy, regardless of gestational age.

Typical physiological levels (ng/mL) are as follows.

| Women: | |
|---|---|
| Normal Cycling; | |
| Follicular | 0.5 |
| Ovulatory | 0.5–1.5 |
| Luteal | 4.0–20.0 |
| Other; | |
| Prepubertal | 0.2–0.5 |
| Postmenopausal | 0.5 |
| Pregnancy | 40–200 |
| Men: | |
| Prepubertal | 0.25 |
| Adult | 0.25 |

It has been found to be difficult to obtain antibodies that have the appropriate affinity for the analyte relative to the labeled component along with the specificity to allow them to be used effectively in a competitive immunoassay for steroids, such as, for example, estradiol and progesterone. The sources of antibodies are limited in number, thereby resulting in either unavailability or excessively high cost. The use of any but a limited number of antibodies in a competitive assay results in an inadequate dose response, which results in inferior sensitivity, inferior precision, or both of the foregoing. In addition, even when antibodies that demonstrate an appropriate affinity for an analyte can be developed, many of these antibodies may demonstrate the undesirable property of high cross-reactivity to structurally-similar steroids. It would be desirable to provide a competitive immunoassay format capable of detecting levels of estradiol below 50 pg/mL and levels of progesterone below 1 ng/mL, concentrations which are clinically useful but difficult to measure.

The probability that a particular anti-steroid antibody/labeled component pair will be useful to prepare a sensitive assay for a given steroid can be assessed by knowledge of the dose response curve. The dose response curve for asteroid assay is a plot of the ratio of the rate of production of response in the presence of steroid analyte to the rate of production of response in the absence of steroid analyte as a function of the concentration of the steroid analyte. The dose response curve for a given steroid assay is unique for each antibody/labeled component combination used and is modulated by the competition between antibody analyte and labeled component. Consequently, for any particular anti-steroid antibody/labeled component/steroid analyte combination, a relatively steep dose response curve indicates that the particular combination will be more likely to provide a clinically useful assay.

SUMMARY OF THE INVENTION

This invention provides a method and kit for measurement of a steroid by means of a competitive immunoassay, preferably a competitive enzyme immunoassay. The method and kit involve the use of asteroid analogue conjugated to a label. The steroids that are amenable to detection by the method and kit of the present invention include estradiol and progesterone.

The method comprises the steps of:

a. incubating a mixture of a test sample suspected of containing a given steroid, a solid phase coupled to an antibody specific for that steroid, and a conjugate of an analogue of that steroid to form steroid/antibody complexes and conjugate/antibody complexes on said solid phase;

b. separating said solid phase from said mixture;

c. measuring the amount of label present in said mixture or in said solid phase; and d. determining the amount of steroid in said sample from the amount of label.

The kit comprises a solid phase coupled to an antibody specific for a steroid and a conjugate of an analogue of that steroid.

The steroid analogues that are preferred for use in the present invention can be represented by the following structural formulae:

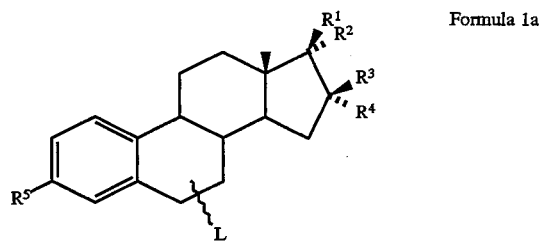

Formula 1a where $R^1$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^2$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^3$ represents a member selected from the group consisting of OH, H, an alkyl group, preferably having 1 to 3 carbon atoms, an alkenyl group, preferably having 2 to 3 carbon atoms, and an alkynyl group, preferably having 2 to 3 carbon atoms, and an alkoxy group, preferably having 1 to 3 carbon atoms;

$R^4$ represents a member selected from the group consisting of OH, H, an alkyl group, preferably having 1 to 3 carbon atoms, an alkenyl group, preferably having 2 to 3 carbon atoms, and an alkynyl group, preferably having 2 to 3 carbon atoms, and an alkoxy group, preferably having 1 to 3 carbon atoms;

$R^5$ represents an alkoxy group; preferably having 1 to 3 carbon atoms, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom.

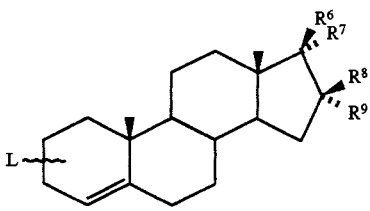

Formula 1b where $R^6$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^7$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^8$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^9$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom.

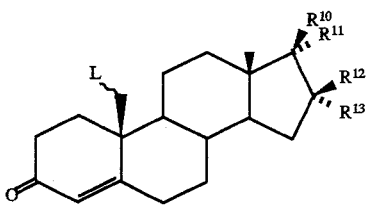

Formula 1c where $R^{10}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^{11}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^{12}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^{13}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom.

In the Formulae 1a, 1b, and 1c, the label group (∼∼L) is represented as being attached to a specific ring or to a specific radical. However, it is to be understood that the label group can be attached to the compound at any position where attachment is possible. Positions of possible attachment are well known to those of ordinary skill in the art.

The preferred substituents for Formula 1a include H for $R^1$, OH for $R^2$, H for $R^3$, H for $R^4$, and OH for $R^5$ or OH for $R^1$, —C≡CH for $R^2$, H for $R^3$, H for $R^4$, and OH for $R^5$; the preferred substituents for Formula 1b include —CH(OH)CH$_3$ for $R^6$, H for $R^7$, H for $R^8$, and H for $R^9$; the preferred substituents for Formula 1c include OH for $R^{10}$, H for $R^{11}$, H for $R^{12}$, and H for $R^{13}$.

The primary benefit of the present invention is that the performance of a given antibody can be improved over that obtainable when it is used in a conventional assay format, i.e., when the steroid moiety of the conjugate is of the same chemical structure as the analyte. Heretofore unacceptable antibodies, i.e., antibodies that provide inadequate dose response curves, can now perform satisfactorily in a competitive immunoassay where an analogue of the analyte is used in the conjugate, where either the substituents of the steroid moiety of the conjugate are different or the position of the label is different or both the substituents of the steroid moiety of the conjugate and the position of the label are different.

DETAILED DESCRIPTION

Figure 1:
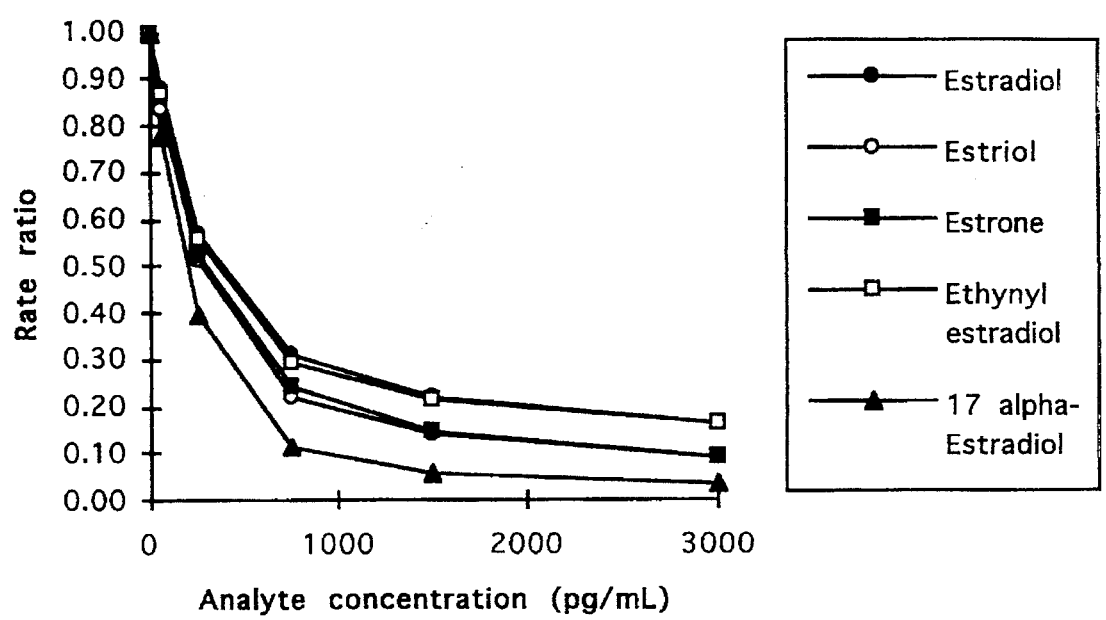
FIG. 1 is a graph illustrating the dose response curves of various estrogen-alkaline phosphatase conjugates with anti-estradiol antibody.

The method of the present invention comprises the steps of a. incubating a mixture of a test sample suspected of containing a given steroid, a solid phase coupled to an antibody specific for that steroid, and a conjugate of an analogue of that steroid to form steroid/antibody complexes and conjugate/antibody complexes on said solid phase;

b. separating said solid phase from said mixture;

c. measuring the amount of label present in said mixture or in said solid phase; and d. determining the amount of steroid in said sample from the amount of label.

The kit of the present invention comprises a solid phase coupled to an antibody specific for asteroid and a conjugate of an analogue of that steroid.

As used herein, an "analogue" of a given analyte, i.e., a steroid, is a chemical compound that is structurally similar to the analyte, but differs from the analyte with respect to at least one of the following:

(1) the orientation of at least one substituent (e.g., α-OH for β-OH);

(2) the identity of a given substituent (e.g., —C≡CH for —H); or (3) the degree of unsaturation of a ring of the steroid backbone (e.g., a benzene, cyclohexene, or cyclohexane ring for the A ring of the steroid).

The A, B, C, and D rings of the cyclopentanophenanthrene ring, which forms the backbone of the steroid, are labeled in FIG. 10.22 of *Textbook of Biochemistry with Clinical Correlations,* Second Edition, edited by Thomas M. Devlin, John Wiley & Sons, Inc. (1986), page 402, incorporated herein by reference.

In the case of the analyte estradiol, representative examples of estradiol analogues include, but are not limited to, those compounds wherein at least one of the following modifications has been made:

(a) β-OH at position 17 is replaced by α-OH;

α-H at position 17 is replaced by the ethynyl group (—C≡CH);

(c) α-H at position 16 is replaced by α-OH; or (d) the degree of unsaturation in the A ring is changed to provide a 3-keto-4-ene, a methyl group is added to the junction of the A ring and the B ring at position 10, and the label is attached to the aforementioned methyl group at position 19.

However, in the case of the estradiol analogues, at position 17, the substituents OH and H cannot be replaced by any substituent attached to the carbon atom at position 17 by a double bond (e.g., =O or =N).

In the case of the analyte progesterone, representative examples of progesterone analogues include, but are not limited to, those compounds wherein at least one of the following modifications has been made:

(a) =O at position 20 is replaced by both β-H and α-OH;

(b) α-H at position 17 is replaced by α-OH; or (c) the degree of unsaturation in the A ring is changed to provide a 3-hydroxy substituted triene, the methyl group is removed from the junction of the A ring and the B ring at position 10, the β-COCH$_3$ at position 17 is replaced by β-H, and the α-H at position 17 is replaced by α-OH.

With respect to the substituent(s) on the estradiol analogue at position 17, the β-OH substituent of the estradiol compound can be replaced by an α-OH substituent. However, the carbon atom at position 17 of the estradiol analogue does not contain two substituents that are attached to the carbon atom at position 17 by an oxygen atom. For example, the carbon atom at position 17 does not have two —OH substituents. The substituent(s) at position 17 can differ from the —OH substituent of the estradiol compound. The substituent(s) at position 17 of the estradiol analogue can be an alkyl group, preferably having from 1 to 3 carbon atoms, an alkenyl group, preferably having from 2 to 3 carbon atoms, an alkynyl group, preferably having from 2 to 3 carbon atoms, and alkoxy group, preferably having from 1 to 3 carbon atoms. The alkyl group, the alkenyl group, the alkynyl group, or the alkoxy group can be unsubstituted or substituted. However, the substituent attached to the carbon atom at position 17 is not a group that is attached to the carbon atom at position 17 by a double bond. In other words, the substituent at position 17 is not =O, =N—, or the like. With respect to the substituent(s) on the estradiol analogue at position 16, the substituent(s) can be the same as those substituent(s) that can be located at position 17. The prohibitions for the substituent(s) at position 16 are the same as those for the substituent(s) at position 17. The precise nature of the substituents on the aforementioned alkyl, alkenyl, alkynyl, and alkoxy groups is not critical. However, they must not adversely affect the immunoassay in which the analyte analogue will be employed. Representative examples of such substituents include, but are not limited to, the hydroxyl group and alkyl groups.

As used herein, the expression "label group" means a group attached to an antibody or an analyte or an analyte analogue to render the reaction between the antibody and the analyte or analyte analogue detectable. Representative examples of labels include enzymes, radioactive labels, fluorescein, and chemicals that produce light. A label is any substance that can be attached to asteroid or a derivative of asteroid and that is capable of producing a signal that is detectable by visual or instrumental means. Various labels suitable for use in this invention include catalysts, enzymes, liposomes, and other vesicles containing signal producing substances such as chromogens, catalysts, fluorescent compounds, chemiluminescent compounds, enzymes, and the like. A number of enzymes suitable for use as labels are disclosed in U.S. Pat. No. 4,275,149, incorporated herein by reference. Such enzymes include glucosidases, galactosidases, phosphatases and peroxidases, such as alkaline phosphatase and horseradish peroxidase, which are used in conjunction with enzyme substrates, such as fluorescein di(galactopyranoside), nitro blue tetrazolium, 3,5',5,5'-tetranitrobenzidine, 4-methoxy-1-naphthol, 4-chloro-1-naphthol, 4-methylumbelliferyl phosphate, 5-bromo-4-chloro-3-indolyl phosphate, chemiluminescent enzyme substrates, such as the dioxetanes described in WO 88100694 and EP 0-254-051-A2, and derivatives and analogues thereof. Preferably, the label is an enzyme and most preferably the enzyme is alkaline phosphatase. This invention involves a method and a kit for detecting and measuring a steroid in biological fluids.

The term "test sample", as used herein, refers to a material suspected of containing the analyte. The test sample can be used directly as obtained from the source or following a pretreatment to modify the character of the sample. The test sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The test sample can be pretreated prior to use, such as preparing plasma from blood, diluting viscous fluids, and the like. Methods of treatment can involve filtration, distillation, extraction, concentration, inactivation of interfering components, the addition of reagents, and the like. Other liquid samples besides physiological fluids can be used, such as water, food products, and the like, for the performance of environmental or food production assays. In addition, a solid material suspected of containing the analyte can be used as the test sample. In some instances it may be beneficial to modify a solid test sample to form a liquid medium or to release the analyte.

Steroids that have been found to be particularly useful as analytes include, but are not limited to, estradiol, progesterone, testosterone, and derivatives of the foregoing.

Compounds that have been found to be particularly suitable for use in step (a) can be analogues of estradiol, analogues of progesterone, and analogues of testosterone.

The steroid analogues that are preferred for use in the present invention can be represented by the following structural formulae:

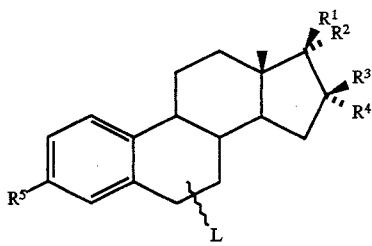

Formula 1a where $R^1$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^2$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^3$ represents a member selected from the group consisting of OH, H, an alkyl group, preferably having 1 to 3 carbon atoms, an alkenyl group, preferably having 2 to 3 carbon atoms, and an alkynyl group, preferably having 2 to 3 carbon atoms, and an alkoxy group, preferably having 1 to 3 carbon atoms;

$R^4$ represents a member selected from the group consisting of OH, H, an alkyl group, preferably having 1 to 3 carbon atoms, an alkenyl group, preferably having 2 to 3 carbon atoms, and an alkynyl group, preferably having 2 to 3 carbon atoms, and an alkoxy group, preferably having 1 to 3 carbon atoms;

$R^5$ represents an alkoxy group, preferably having 1 to 3 carbon atoms, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom.

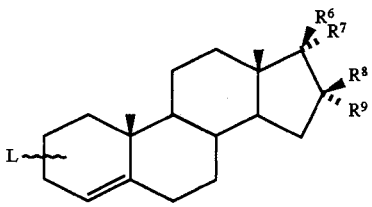

Formula 1b where $R^6$ represents a member selected from the group consisting of OH, H, an alkyl group, preferably having 1 to 3 carbon atoms, an alkenyl group, preferably-having 2 to 3 carbon atoms, an alkynyl group, preferably having 2 to 3 carbon atoms, and an alkoxy group, preferably having 1 to 3 carbon atoms;

$R^7$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^8$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^9$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

L represents a label group; provided that the carbon atom at position 16 does not contain two substituents that are attached to the carbon atom at position 16 by an Oxygen atom, and further provided that the carbon atom at position 17 does not contain two substituents that are attached to the carbon atom at position 17 by an oxygen atom.

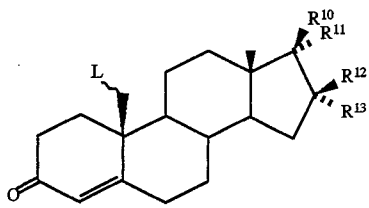

Formula 1c where $R^{10}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group; preferably having 1 to 3 carbon atoms;

$R^{11}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^{12}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

$R^{13}$ represents a member selected from the group consisting of OH, H, an alkyl group, preferably having 1 to 3 carbon atoms, an alkenyl group, preferably having 2 to 3 carbon atoms, an alkynyl group, preferably having 2 to 3 carbon atoms, and an alkoxy group, preferably having 1 to 3 carbon atoms;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom.

Representative examples of analogues of estradiol suitable for use in the method and kit of this invention can be represented by the following structural formulae:

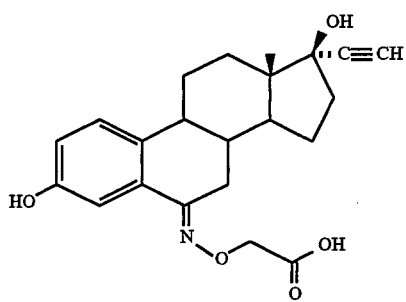

1,3,5,[10]-Estratrien-
17α-ethynyl-3,17β-
diol-6-one 6-CMO(EE2)

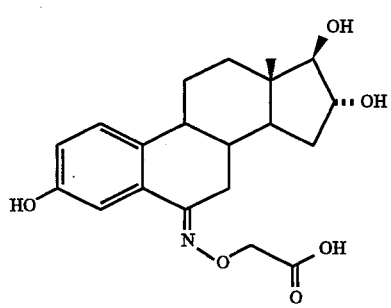

1,3,5,[10]-Estratrien-
3,16α,17β-triol-6-one 6-
CMO(E3)

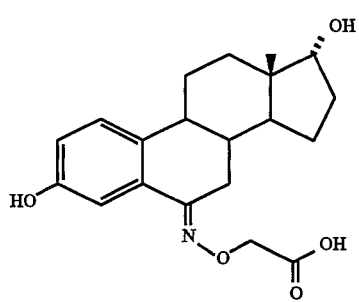

1,3,5,[10]-Estratrien-
3,17α-diol-6-one 6-
CMO(17aE2)

Representative examples of analogues of progesterone suitable for use in the method and kit of this invention can be represented by the following structural formulae:

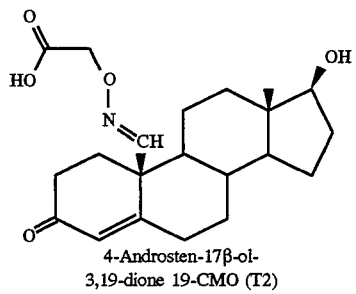

4-Androsten-17β-ol-
3,19-dione 19-CMO (T2)

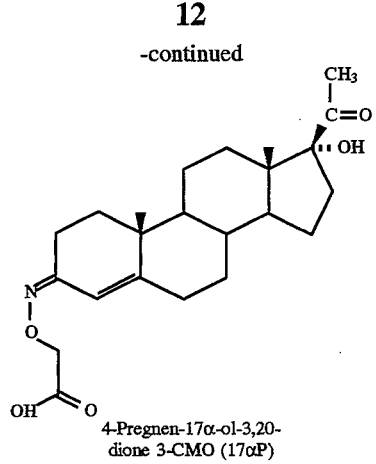

4-Pregnen-17α-ol-3,20-
dione 3-CMO (17αP)

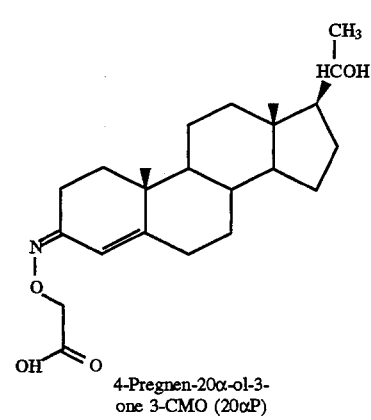

4-Pregnen-20α-ol-3-
one 3-CMO (20αP)

In general, the substituents most preferred for the analogues of estradiol are β-OH and α-C≡CH at position 17, β-H and α-H at position 16, and —OH at position 3, or β-OH and α-H at position 17, β-H and α-OH at position 16, and —OH at position 3, or β-H and α-OH at position 17, β-H and α-H at position 16, and —OH at position 3. The substituents most preferred for the analogues of progesterone are β-CH(OH)CH3 and α-H at position 17 and α-H and β-H at position 16 or β-C(O)CH3 and a-OH at position 17 and α-H and β-H at position 16.

The analogues can be prepared by procedures that are well known to one of ordinary skill in the art. The conjugate is preferably prepared by coupling the label to the conjugate precursor. Conjugate precursors are commercially available. Many analogues, such as, for example, the six representative examples shown above, are commercially available.

Steroid analytes such as estradiol, progesterone, testosterone, prednisone, and cortisone can be detected and measured by common immunoassay formats. However, for the sake of brevity, only the estradiol immunoassay techniques will be described in detail. However, one of ordinary skill in the art will appreciate that progesterone, testosterone, prednisone, and cortisone, and other steroids, both naturally occurring and synthetic, can be detected and measured by techniques that are substantially similar to the techniques that will now be described in detail.

Binding members specific for estradiol include estradiol-specific binding proteins, such as monoclonal and polyclonal antibodies and other estradiol specific synthetic or recombinant proteins that specifically bind estradiol. For example, it is well known by those skilled in the art that monoclonal and polyclonal antibodies that specifically bind to steroids such as estradiol can be produced. When an immunogen comprising estradiol or a derivative of estradiol coupled to a carrier protein (e.g.; albumin), typically by a covalent bond, is injected into an animal, the animal's immune system will produce polyclonal antibodies that specifically bind to estradiol. General methods for the preparation of monoclonal antibodies to analytes using mice or rats are well known to those skilled in the art. More recently methods for preparing analyte specific synthetic and recombinant proteins have been reported, and the same methods can be readily adapted to the preparation of estradiol specific synthetic and recombinant proteins that are useful in this invention.

Preferably, estradiol is measured by using a solid phase having a binding member specific for estradiol bound thereto. An example of a solid phase is a microparticle. The solid phase and the test sample are separated so that the amount of steroid conjugate bound to the solid phase or the amount of steroid conjugate remaining in solution can be determined. Preferably, the amount of steroid conjugate bound to the solid phase or the amount of steroid conjugate remaining in solution is determined by enzyme immunoassay, wherein an enzyme is used as the label in the conjugate. A material referred to as an enzyme substrate can be converted into a fluorescent compound, such as 4-methylumbelliferone, by an appropriate enzyme. The rate at which the fluorescent compound is formed is an indication of the quantity of enzyme present in the reaction mixture. When the enzyme is a label, as in an enzyme immunoassay, the quantity of enzyme present is related to the quantity of estradiol present in the test sample. Thus, the measurement of fluorescence can be used to determine to the quantity of estradiol present in the test sample. The amount of steroid conjugate on the solid phase or in solution can be correlated to the concentration of estradiol in the test sample by means of a plot showing enzyme activity as a function of estradiol concentration, typically referred to as a standard curve. A standard curve can be prepared by performing the assay using calibrators such as those set forth in Table I, which will be discussed later. Controls are used to verify that the standard curve is valid. When a sample having an unknown estradiol level is assayed, the measured assay signal is compared to the standard curve, and the estradiol level corresponding to the measured signal is the estradiol level of the sample.

The specific binding member may be bound to the solid phase by physical or chemical means, preferably by means of a covalent bond. The specific binding member should be bound to the solid phase in such a way that substantially none of the specific binding members detach during the subsequent reactions and wash steps. Regardless of the specific binding member and the coupling method selected, the specific binding member must be able to bind to estradiol and to the steroid conjugate after being coupled to the solid phase.

A solid phase according to the present invention may be a mixture of microparticles with binding members specific for estradiol chemically or physically bound to the microparticles. Microparticles that can be used in this invention are preferably made of polymeric material, and more preferably include microparticles derived from polymers having styrene units or polymers having acrylate units. The microparticles are preferably substantially spherical and preferably have radii ranging from about 0.1 μm to about 0.25 inches. A preferred method for separating these particles from the test sample involves capture of the microparticle on a porous matrix, such as a glass fiber.

Other solid phases that can be used include a mixture of magnetizable microparticles having binding members specific for estradiol chemically or physically bound to the microparticles. Magnetizable microparticles that are useful in this invention preferably have ferric oxide or chromium oxide cores and a polymeric coating. Such coatings are preferably made from homopolymers and copolymers having styrene units, homopolymers and copolymers having carboxylated styrene units, or homopolymers and copolymers having acrylate or methacrylate units. Other solid phases that are known to those skilled in the art include the walls of wells of reaction trays, tubes, polymeric beads, nitrocellulose strips, membranes, and the like. Natural, synthetic, and naturally occurring materials that are synthetically modified can be used as the material of the solid phase. Such materials include polysaccharides, e.g., cellulosic materials, such as, for example, paper and cellulosic derivatives, such as cellulose acetate and nitrocellulose; silica; inorganic materials, such as, for example, deactivated alumina, diatomaceous earth, $MgSO_4$, or other inorganic finely divided material uniformly dispersed in a porous polymeric matrix, wherein the matrix may comprise one or more polymers such as homopolymers and copolymers of vinyl chloride, e.g., polyvinyl chloride, vinyl chloride-propylene copolymer, and vinyl chloride-vinyl acetate copolymer; cloth, both naturally occurring (e.g., cotton) and synthetic (e.g., nylon); porous gels, such as silica gel, agarose, dextran, and gelatin; polymeric films, such as polyacrylamide; and the like. In any case, the solid phase should have sufficient strength to maintain the desired physical shape and should not interfere with the production of a detectable signal. Strength can be provided by means of a support.

An alternative separation method is described in U.S. patent application Ser. Nos. 150,278, abandoned, filed Jan. 20, 1988 and 375,029, abandoned, filed Jul. 7, 1989, both of which enjoy common ownership and both of which are incorporated herein by reference. A published counterpart of this reference is WO 92/21980, published Dec. 10, 1992, incorporated herein by reference. These references describe a method involving ion capture separation, in which the specific binding members used in the assay are chemically attached to both a first polyionic compound and to a porous matrix having bound thereto a second polyionic compound that binds to the first polyionic compound. A specific binding pair is formed and separated from the reaction mixture by an electrostatic interaction between the first and second polyionic compounds. A specific binding member of the specific binding pair is preferably covalently coupled to the first polyionic compound.

Preferably, the first polyionic compound is a polyanionic acid, such as polyaspartic acid, heparin, carboxylmethyl amylose, polyglutamic acid, or polyacrylic acid, and the second polyionic compound is a cationic polymer, such as a polymeric quaternary ammonium compound ("GafQuattum", GAF Corporation, Wayne, N.J., 07470), diethylaminoethyl-dextran (Sigma Chemical Company, St. Louis, Mo.), water soluble cellulose derivatives, such as those having the trademarks "Celquat L-200" and "Celquat H-100" (National Starch & Chemical Corporation, Bridgewater, N.J. 08807), both of which are polymeric quaternary compounds, or Merquat® 100 (Calgon Corporation). The porous matrix is treated with the cationic polymer to provide a positive charge to the matrix. The cationic polymer is bound to the matrix by absorption, adsorption, or covalent or ionic coupling. The separation of the reaction products is effected by the electrostatic interaction between the positively-charged matrix and the negatively-charged polyanion complex.

A porous matrix suitable for use in this invention can be any suitable porous material. As used herein, "porous material" means a material through which fluids can flow and can easily pass. Representative examples of materials suitable for the porous matrix include, but are not limited to, olefin polymers, e.g., polypropylene, polyethylene, fluorinated olefin polymers, e.g., polytetrafluorethylene, fiberglass, cellulose, or nylon.

Preferred materials for the porous matrix include a porous fiberglass material, such as a "Whatman 934-AH" filter paper, which has a nominal thickness of 0.33 mm, or the disposable IMx® cartridge and TestPack™ (fiber matrix) devices (Abbott Laboratories, Abbott Park, Ill.; 60064). The thickness of such material is not critical, and will be a matter of choice, based upon the properties of the test sample or analyte being assayed, such as the fluidity of the test sample.

As stated previously, an enzyme substrate can be converted into a fluorescent compound, such as 4-methylumbelliferone, by an appropriate enzyme. The rate at which the fluorescent compound is formed is an indication of the quantity of enzyme present in the reaction mixture. When the enzyme is a label, the quantity of enzyme present is related to the quantity of estradiol present in the test sample. Thus, the measurement of fluorescence resulting from enzyme activity in an enzyme immunoassay can be used to determine to the quantity of estradiol present in the test sample. Fluorescence can be measured by any method known to the art. For example, a fluorescence spectrometer can be used. The fluorescence spectrum can also be observed by means of a visual spectrometer or by a photograph with a spectrograph of high light-gathering power.

In a preferred embodiment, the fluorescence can be detected by using an IMx® automated bench top analyzer (Abbott Laboratories, Abbott Park, Ill.). This analyzer contains an optical assembly comprising a fluorometer that uses a mercury arc lamp as its light source. This instrument is described by Fiore et al (Clin. Chem., 34/9:1726–1732, 1988), incorporated herein by reference. The instrument utilizes IMx® disposable cartridges (commercially available from Abbott Laboratories, Abbott Park, Ill.), which contain a porous matrix to capture microparticles containing anti-estradiol antibodies that have been exposed to a conjugate and the sample. The label used in the conjugate is preferably alkaline phosphatase. The estradiol in the sample binds to anti-estradiol antibodies on the microparticles. The microparticles are separated from the reaction mixture, conjugate is added to the microparticles, conjugate binds to available anti-estradiol antibodies, and the quantity of conjugate present on the microparticles is determined from the rate at which 4-methylumbelliferyl phosphate is converted into 4-methylumbelliferone. The quantity of estradiol in the sample can be determined from a standard curve of rate of 4-methylumbelliferone formation as a function of estradiol concentration. The standard curve is also known as a calibration curve.

The standard curve that relates the rate of 4-methylumbelliferone formation to estradiol concentration is generally prepared from calibrator solutions containing known estradiol concentrations. Preferably, six calibrators are used to obtain a calibration curve, though more or fewer calibrators can be used, depending on the accuracy and precision of the result desired. Preferably, the calibrators contain increasing amounts of estradiol. For example, Table I illustrates the compositions of one set of calibrators, i.e. for IMx® Estradiol assay. Controls are generally used in conjunction with an assay to confirm the validity of a calibration curve or assay reagents. The formulation of the controls may be different from that of the calibrators, and the estradiol concentration of a given control may not be identical with that of any one of the calibrators. For example, controls having an estradiol concentration of 150, 500, and 1125 pg/mL would be suitable controls for the calibrators in Table I. One skilled in the art would be capable of devising other calibrator and control formulations.

TABLE I

| Calibrator | Estradiol concentration (pg/mL) |
|---|---|
| F | 3000 |
| E | 1500 |
| D | 750 |
| C | 250 |
| B | 50 |
| A | 0 |

To maintain aseptic conditions throughout the procedure, it may be desirable to add small quantity of an anti microbial agent to the system which may include solvents, antibiotics and poisons.

The following examples are illustrative of the invention and are not to be interpreted as limiting the scope of the invention, as defined in the claims. All percentages are by grams (g) weight per 100 milliliters (mL) volume (w/v), unless otherwise indicated.

EXAMPLE 1

Estradiol Assay

Estradiol assays were performed on IMx® disposable cartridges by an IMx® instrument according to the following procedure. A serum sample (75 μL) was mixed with IMx® Estradiol Assay buffer (35 μL), IMx® Estradiol microparticles coated with anti-estradiol antibody (50 μL), and IMx® Buffer (90 μL) to form a reaction mixture. The reaction mixture was incubated for 27.5 minutes at a temperature of 35° C.

IMx® Estradiol Assay buffer was composed of 5α-dihydrotestosterone (2 μg/mL), 0.75% (w/v) saponin, 0.5 M glycine, 0.25 mM sodium citrate, and 0.12% methyl isothiazolinone (w/v), all at pH 4.5. IMx® Estradiol microparticles coated with anti-estradiol antibody (0.005–0.02% solids, w/v) were suspended in IMx® Estradiol Assay buffer, which was composed of 0.1 M bis-(2-hydroxyethyl) iminotris(hydroxymethyl) methane (hereinafter "Bis-Tris"), 0.1 M sodium chloride, 13.6% sucrose (w/v), 0.1% sodium azide (w/v), and 0.2 mg/mL normal rabbit IgG, all at pH 6.5. IMx® Buffer was composed of 0.3 M NaCl, 0.1 M tris (hydroxymethyl)amino methane (hereinafter "Tris"), 0.1% sodium azide (w/v), all at pH 7.5.

One hundred seventy five microliters (175 μL) of the reaction mixture were transferred to the fiber matrix of an IMx® disposable cartridge. The fiber matrix was located over an absorbent pad of the IMx® cartridge. The microparticles were captured by the fiber matrix, and the solution was absorbed by the absorbent pad. The microparticles were then washed with IMx® Buffer. A steroid-alkaline phosphatase conjugate (60 μL) was added to the matrix, incubated for 12 seconds at a temperature of 35° C., and then washed again with IMx® Buffer. The conjugate (2–8 μg/mL alkaline phosphatase) was in conjugate buffer composed of 0.1 M Bis-Tris, 0.5 M sodium chloride, 1% casein (w/v), 1 mM magnesium chloride, 0.1 mM zinc chloride, 0.1% azide (w/v), all at pH 6.5. The preparation of various steroid-alkaline phosphatase conjugates is described in Example 4.

A 1.2 mM solution of 4-methylumbelliferone phosphate (65 μL) in 0.1 M 2-amino-2-methyl-1-propanol buffer, at pH 9, was added to the matrix, and the rate of 4-methylumbelliferone formation was measured by fluorescence reflectance. The IMx® instrument measured fluorescence with a fluorometer that used a mercury arc lamp as its light source, as described in Fiore et al., Clin. Chem., 34/9: 1726–1732, 1988, the contents of which were previously incorporated by reference.

Materials needed for the assay, including IMx® Estradiol buffer, IMx® Estradiol anti-estradiol antibody coated microparticles, conjugate, methylumbelliferone phosphate substrate, IMx® Buffer, IMx® disposable cartridges, and IMx® instruments are available commercially from Abbott Laboratories, Abbott Park, Ill. and are described in U.S. Pat. No. 5,342,760, European Application No. EP-A-288 793, and in Fiore et al., Clin. Chem. 34/9: 1726–1732, 1988, all of which are incorporated herein by reference.

EXAMPLE 2

Progesterone Assay

Progesterone assays were performed on IMx® disposable cartridges by an IMx® instrument according to a procedure similar to that used in the estradiol assay in Example 1, with the following modifications. A serum sample (50 µL) was mixed with progesterone sample buffer (80 µL), microparticles coated with anti-progesterone antibody (80 µL), and IMx® Buffer (40 µL). The reaction mixture was incubated for 20.8 minutes at a temperature of 35° C.

Progesterone sample buffer was composed of 2.25 M glycine, 5α-dihydrotestosterone (0.5 µg/mL), 0.2% (w/v) saponin (EM Industries, Hawthorne, N.Y.), 0.1 M sodium chloride, and 0.1% methyl isothiazolinone (w/v, Rohm and Haas, Philadelphia, Pa.), all at pH 2.8. The microparticles (Seradyne, Indianapolis, Ind.) coated with anti-progesterone antibody (BiosPacific, Emeryville, Calif.) contained 0.003% (w/v) solids suspended in a buffer that contained 0.5 M morpholinoethanesulphonic acid (MES), 0.1 M sodium chloride, 10% sucrose (w/v), 2% bovine serum albumin (w/v, Intergen, Purchase, N.Y.), 0.1 mg/mL mouse IgG (50% (w/v) ammonium sulfate cut of mouse serum obtained from Stellar Biosysytems, Columbia, Md.), and 0.2% sodium azide (w/v), all at pH 6.5

One hundred seventy five microliters (175 µL) of the reaction mixture were transferred to the fiber matrix of an IMx® disposable cartridge. The microparticles were then washed with IMx® Buffer. A steroid-alkaline phosphatase conjugate (60 µL) was added to the matrix, the reaction was incubated for 8 seconds at a temperature of 35° C., and then washed again with IMx® Buffer. The conjugate (2–15 µg/mL alkaline phosphatase) was in a buffer composed of 50 mM Tris, 100 mM sodium chloride, 10 mM magnesium chloride, 0.1 mM zinc chloride, 0.5% casein (w/v, Sigma Chemical Company, St. Louis, Mo.), and 0.1% sodium azide (w/v), all at pH 7.4.

The addition of 4-methylumbelliferone phosphate and measurement of the rate of 4-methylumbelliferone formation was carried out according to the method described in Example 1.

EXAMPLE 3

Preparation of Antibody-Coated Microparticles

Microparticles coated with antibody were prepared as follows:

a. Murine anti-estradiol monoclonal antibodies (BiosPacific A3268; Biogenesis 2F-9, Sandown N.H.; Medix MBE 0107, San Carlos, Calif.) and the anti-progesterone monoclonal antibody (BiosPacific 087) were obtained from vendors. Anti-estradiol polyclonal antibodies (BiosPacific B4996 and Medix M17794) were also obtained from a vendor.

b. Rabbit anti-estradiol polyclonal antibodies were prepared by injecting rabbits with estradiol 6-(O-carboxymethyl)oxime (Sigma Chemical Company, St. Louis, Mo. and Steraloids, Wilton, N.H.) coupled to bovine serum albumin in Freund's complete adjuvant and boosting with Freund's incomplete adjuvant.

c. Latex microparticles (sufficient for a final reaction concentration of 1% solids, w/v) were mixed with 50 mM MES buffer (pH 4.5) and antibody at 1 mg/mL. 1-Ethyl-3-(3-dimethylaminopropyl) carbodiimide (EDAC) was added to give a final concentration of 0.5 mg/mL. After the mixture was incubated for 30 minutes at room temperature, the microparticles were washed three times with 0.1 M Tris (pH 7.4) containing 0.1% "Tween 20" surfactant (v/v) and 0.1 M sodium chloride. The microparticles were then resuspended in microparticle storage buffer. The anti-estradiol antibody-coated microparticle storage buffer is described in Example 1, and the anti-progesterone antibody-coated microparticle storage buffer is described in Example 2. Assays formulated with these microparticles are described in Example 5.

EXAMPLE 4

Preparation of Steroid-Alkaline Phosphatase Conjugates

Steroid alkaline-phosphatase conjugates were prepared as follows:

a. Ten micrograms (10 µg) of steroid derivative used for a particular conjugation and-10 µg of N-hydroxysuccinimide were dissolved in 100 microliters (100 µL) of dimethylformamide (anhydrous). Forty micrograms (40 µg) of EDAC was added to the solution. The steroids used to produce various conjugates utilizing estradiol analogues and progesterone analogues with calf intestinal alkaline phosphatase are listed in Table II.

b. An aliquot of the mixture in step a was added to alkaline phosphatase (available from Boehringer Mannheim, Germany) in carbonate buffer at pH 8 so that the molar ratio of steroid to enzyme was 10:1 (20:1 for testosterone). The resulting steroid-alkaline phosphatase conjugate was separated from unbound steroid and other low molecular weight materials on a G25 Sephadex column. Aliquots of the separated conjugate were drawn, and these aliquots were diluted to a concentration of approximately 1 to 20 µg/mL in either the estradiol or progesterone conjugate buffers. Example 1 describes the conjugate buffer used in estradiol assays and the assay employing the IMx® instrument. Example 2 describes the conjugate buffer used in progesterone assays and the assay employing the IMx® instrument.

TABLE II

| Steroid | Derivative used for conjugation | Symbol | Catalog | Vendor |
|---|---|---|---|---|
| Estradiol | 1,3,5,[10]-Estratrien-3,17β3 diol-6-one 6-CMO[1] | E2 | K2126 | A[2] |
| Estrone | 1,3,5,[10]-Estratrien-3-ol-6, 17-dione 6-CMO | E1 | E2055 | B[3] |
| Estriol | 1,3,5,[10]-Estratrien-3,16α, 17β-triol-6-one 6-CMO | E3 | K2501 | A |

TABLE II-continued

| Steroid | Derivative used for conjugation | Symbol | Catalog | Vendor |
|---|---|---|---|---|
| Ethynyl estradiol | 1,3,5,[10]-Estratrien-17α-ethynyl-3,17β-diol-6-one 6-CMO | EE2 | E1582 | B |
| 17α-Estradiol | 1,3,5,[10]-Estratrien-3,17α-diol-6-one 6-CMO | 17αE2 | E1335 | B |
| 20-Hydroxy progesterone | 4-Pregnen-20α-ol-3-one 3-CMO | 20αP | Q3605 | B |
| 17-Hydroxy progesterone | 4-Pregnen-17α-ol-3,20-dione 3-CMO | 17αP | Q3375 | B |
| Testosterone | 4-Androsten-17β-ol 3,19-dione 19-CMO | T2 | 2012-1 | C[4] |

[1]Sigma Chemical Company, St. Louis, MO
[2]Steraloids, Wilton, NH
[3]Research Plus, Bayome, NJ
[4]CMO = [O-carboxymethyl]oxime

EXAMPLE 5

Anti-estradiol Antibody/Steroid Conjugate Matrix

Several anti-estradiol antibodies, including both the murine monoclonal antibodies and rabbit polyclonal antibodies, were tested for rate ratio value with a wide variety of steroid alkaline phosphatase conjugates in the assay format described in Example 1. In addition, an anti-progesterone antibody was tested with three steroid alkaline phosphatase conjugates in the assay format described in Example 2. The results are set forth in Table III.

The dose response is assessed by measuring rate ratio values. As used herein, "rate ratio value" means the quotient obtained by dividing the value of the assay signal observed at a particular analyte concentration (in this example, Table III, Calibrator F) by the value of the assay signal observed with no analyte (in this example, Table III, Calibrator A).

The Abbott IMx® instrument measures the assay signal in units of fluorescent counts per second per second (cps/s). The rate ratio value is a dimensionless number and normalizes the data from different assays, thereby allowing for direct comparison of different assays or assay formats. For convenience, the rate ratio value was calculated from the signals from Calibrator F and from Calibrator A. In the estradiol assay, Calibrator F is at a concentration of 3000 pg/mL estradiol, and in the progesterone assay, Calibrator F is at a concentration of 40 ng/mL progesterone. Calibrator A contains no analyte.

A representative sampling of rate ratio values for the Calibrator F/Calibrator A rates from a screen of over 700 different antibody/steroid conjugate combinations is shown in Table III. Eight steroid conjugates and a representative number of murine monoclonal and rabbit polyclonal antibodies with exceptionally low rate ratio values are illustrated. As an example, for the polyclonal antibody Rabbit 438, the lowest rate ratio value for the eight steroid conjugates tested was for the ethynyl estradiol (EE2) conjugate, where the rate ratio value was 0.20. For all of the 700 antibody/steroid conjugate combinations tested, neither the estradiol nor estrone conjugate generated the best dose response in the estradiol assay. In this example, the estradiol (E2) and estrone (E1) embodiments are comparative examples. They do not constitute analogues for the estradiol assay.

TABLE III[1]

| | E1 | E2 | E3 | E E2 | 17αE2 | 20αP | 17αP | T2 |
|---|---|---|---|---|---|---|---|---|
| Anti-estradiol monoclonal antibodies | | | | | | | | |
| BiosPacific A3268 | 0.20 | 0.25 | 0.14 | 0.23 | 0.45 | 0.94 | nd[2] | nd |
| Biogenesis 2F9 | 0.30 | 0.23 | 0.18 | 0.25 | 0.85 | 1.02 | nd | nd |
| Medix MBE 0107 | 0.57 | 0.69 | 0.50 | 0.48 | 0.26 | 0.38 | 1.02 | 0.77 |
| Anti-estradiol polyclonal antibodies | | | | | | | | |
| Medix M17794 | 0.26 | 0.37 | 0.18 | 0.32 | 0.31 | 1.00 | 0.89 | 0.83 |
| Rabbit 438[3] | 0.38 | 0.41 | 0.37 | 0.20 | 0.37 | 1.07 | 0.89 | 0.57 |
| Rabbit 9959 | 0.40 | 0.50 | 0.39 | 0.30 | 0.47 | 0.84 | 1.09 | 0.55 |
| Rabbit 9969 | 0.45 | 0.53 | 0.44 | 0.31 | 0.35 | 0.92 | 0.81 | 0.94 |
| Rabbit 9965 | 0.21 | 0.27 | 0.16 | 0.17 | 0.13 | 0.85 | nd | nd |
| Rabbit 581 | 0.23 | 0.24 | 0.18 | 0.14 | 0.09 | 0.97 | 0.86 | 0.78 |
| Rabbit 583[4] | 0.09 | 0.16 | 0.09 | 0.16 | 0.03 | 0.84 | 0.87 | 0.43 |
| Rabbit 2522 | 0.73 | 0.69 | 0.67 | 0.62 | 0.61 | 0.22 | 0.99 | 0.39 |
| BiosPacific B4996 | 0.62 | 0.72 | 0.62 | 0.50 | 0.36 | 0.85 | 0.32 | 0.49 |
| Rabbit 2424 | 0.75 | 0.67 | 0.72 | 0.67 | 0.67 | 0.78 | 0.98 | 0.35 |
| Anti-progesterone monoclonal antibody | | | | | | | | |
| BiosPacific 087 | 0.15 | nd | nd | nd | nd | nd | 0.24 | 0.08 |

[1]See Table II for complete name of chemicals denoted by symbols.
[2]not determined
[3]Assignee's rabbits are designated in the following manner: Rabbit ABCD, where A, B, C, and D are numerals.
[4]Antibody used in IMx® Estradiol assay.

EXAMPLE 6

Dose Response Curves for Polyclonal Rabbit 583 Antibodies with Conjugates of Estradiol and Estradiol Analogues The pattern of the rate ratio values for a given steroid assay is unique for each antibody/steroid conjugate combination used, as illustrated in FIGS. 1–6. The rate ratio value is the ratio of the assay signal observed at a particular analyte concentration to the assay signal observed when no analyte is present. The rate ratio value can be measured at any desired analyte concentration. In this example, estradiol calibrators B, C, D, E, and F (from Table I) were used to determine values of rate ratio over the clinically useful range for estradiol concentration. The values of rate ratio for a given antibody/steroid conjugate combination are plotted as a function of the analyte concentration to produce a dose response curve. The dose response curves of selected anti-estradiol antibody/conjugate combinations were assessed over the dynamic range of the IMx® Estradiol assay (0–3000 pg/mL). FIG. 1 demonstrates the different dose response curves observed for the anti-estradiol polyclonal antibody from Rabbit 583 and various estrogen conjugates.

It can be seen that low values of rate ratio for any particular calibrator (e.g., Calibrator F), are associated with steep dose response curves. As used herein, the expression "steep dose response curve" means that a small change in concentration at low concentrations of analyte (i.e., in the abscissa of the curve) results in a large change in the rate ratio value (i.e., in the ordinate of the curve). To further clarify this point, in FIG. 1 the dose response curve for 17αE2 is steeper than the dose response curves for E1 and E3, which curves are steeper than the dose response curves for E2 and EE2. For polyclonal antibody Rabbit 583, the 17αE2 conjugate produced the steepest dose response curve, and similarly the lowest Calibrator F/Calibrator A rate ratio value (0.03). See Table III and FIG. 1. The relative steepness of dose response curves is inversely related to the magnitude of the rate ratio value for Calibrator F (see Table III and Example 5).

A steeper dose response curve in the region of low concentration of analyte makes it possible to obtain a more accurate estimation of analyte concentration in that region. Accordingly, steeper dose response curves for a particular antibody/steroid combination in the region of low concentration of analyte indicate that the combination will provide an immunoassay that can more accurately measure relatively low steroid concentrations, and, consequently, provide a more clinically relevant assay. The accurate measurement of small differences in concentration at low steroid concentrations is considered one of the primary clinical utilities of steroid assays used to diagnose fertility.

EXAMPLE 7

Figure 2:
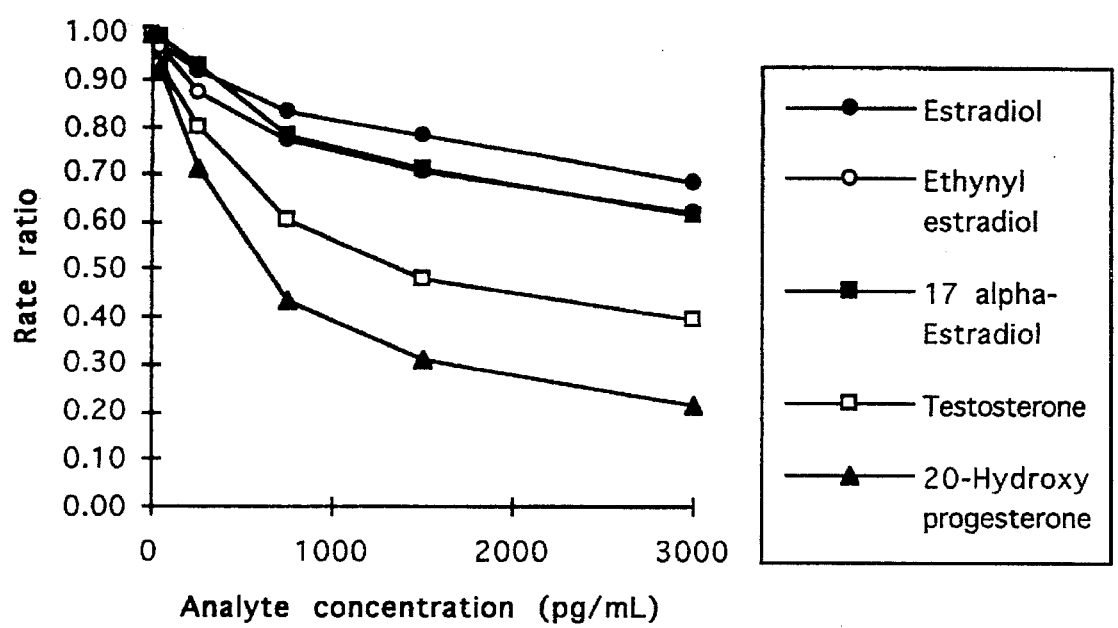
FIG. 2 is a graph illustrating the dose response curves of various steroid-alkaline phosphatase conjugates with anti-estradiol antibody.

Dose Response Curves for Polyclonal Rabbit 2522 Antibodies with Conjugates of Steroid Analogues FIG. 2 illustrates the different dose response curves observed for the anti-estradiol polyclonal antibody from Rabbit 2522 and conjugates of various steroid analogues. For this antibody, the lowest rate ratio value was observed with conjugate haptens other than those containing an aromatic A ring. The dose response curve of progesterone analogue 17αP is steeper than the dose response curve of testosterone T2, which is steeper than the dose response curves of estrogen 17αE2, EE2, and E2.

EXAMPLE 8

Figure 3:
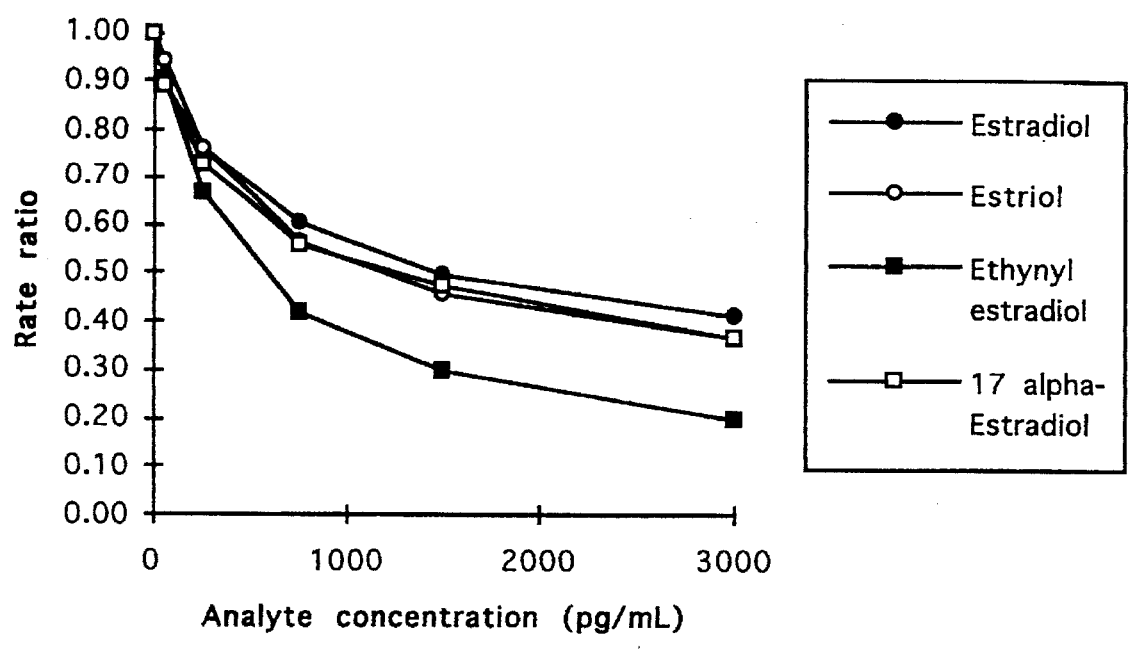
FIG. 3 is a graph illustrating the dose response curves of various estrogen-alkaline phosphatase conjugates with anti-estradiol antibody.

Dose Response Curves for Polyclonal Rabbit 438 Antibodies with Conjugates of Estradiol and Estradiol Analogues FIG. 3 illustrates the different dose response curves observed for the anti-estradiol polyclonal antibody from Rabbit 438 and either conjugate of estradiol or conjugates of various estradiol analogues. For this antibody, the steepest dose response curve was observed with an ethynyl estradiol conjugate hapten (EE2).

EXAMPLE 9

Figure 4:
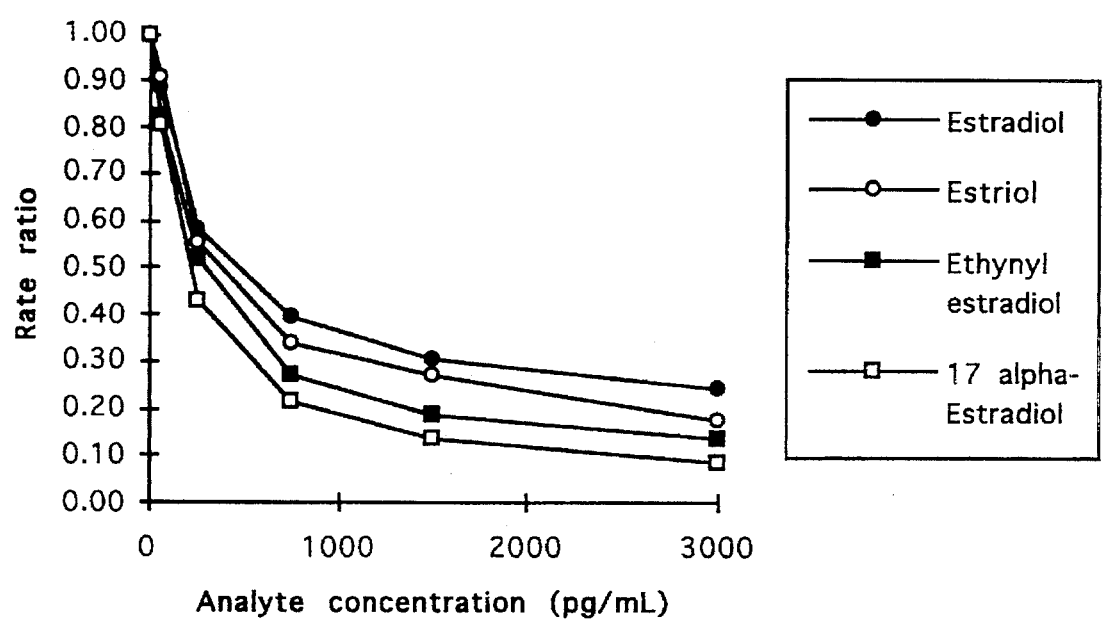
FIG. 4 is a graph illustrating the dose response curves of various estrogen-alkaline phosphatase conjugates with anti-estradiol antibody.

Dose Response Curves for Polyclonal Rabbit 581 Antibodies with Conjugates of Estradiol and Estradiol Analogues FIG. 4 illustrates the different dose response curves observed for the anti-estradiol polyclonal antibody from Rabbit 581 and either conjugates of estradiol or conjugates of various estradiol analogues. For this antibody, the steepest dose response curve was observed with a 17α estradiol conjugate hapten (17α E2).

EXAMPLE 10

Figure 5:
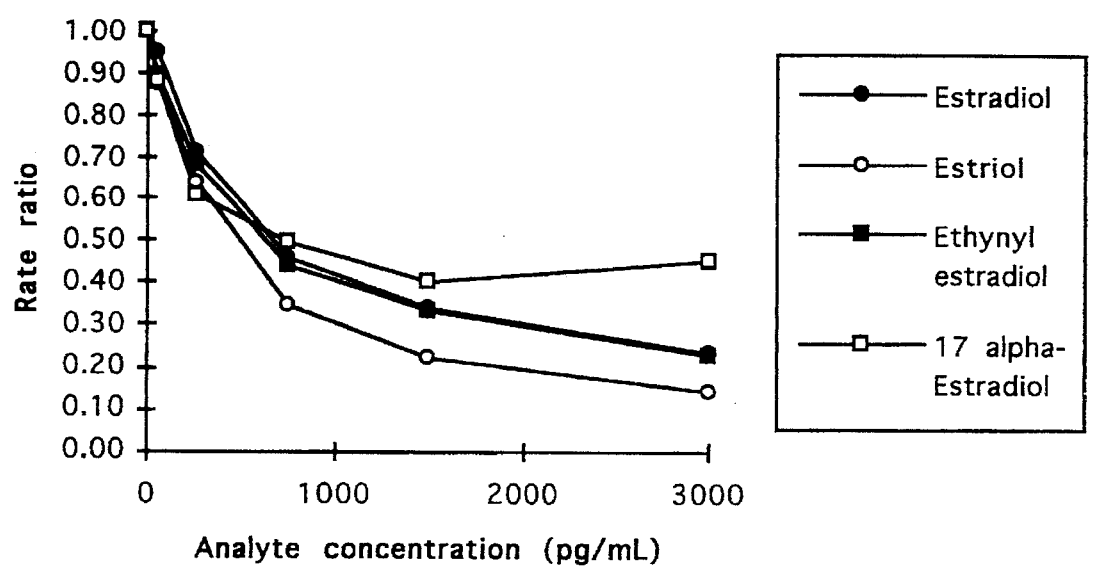
FIG. 5 is a graph illustrating the dose response curves of various estrogen-alkaline phosphatase conjugates with anti-estradiol antibody.

Dose Response Curves for Monoclonal Murine A3268 Antibodies with Conjugates of Estradiol and Estradiol Analogues FIG. 5 illustrates the different dose response curves observed for the anti-estradiol murine monoclonal antibody A3268 from BiosPacific and either conjugate of estradiol or conjugates of various estradiol analogues. For this antibody, the steepest dose response curve was observed with an estriol conjugate hapten (E3).

EXAMPLE 11

Figure 6:
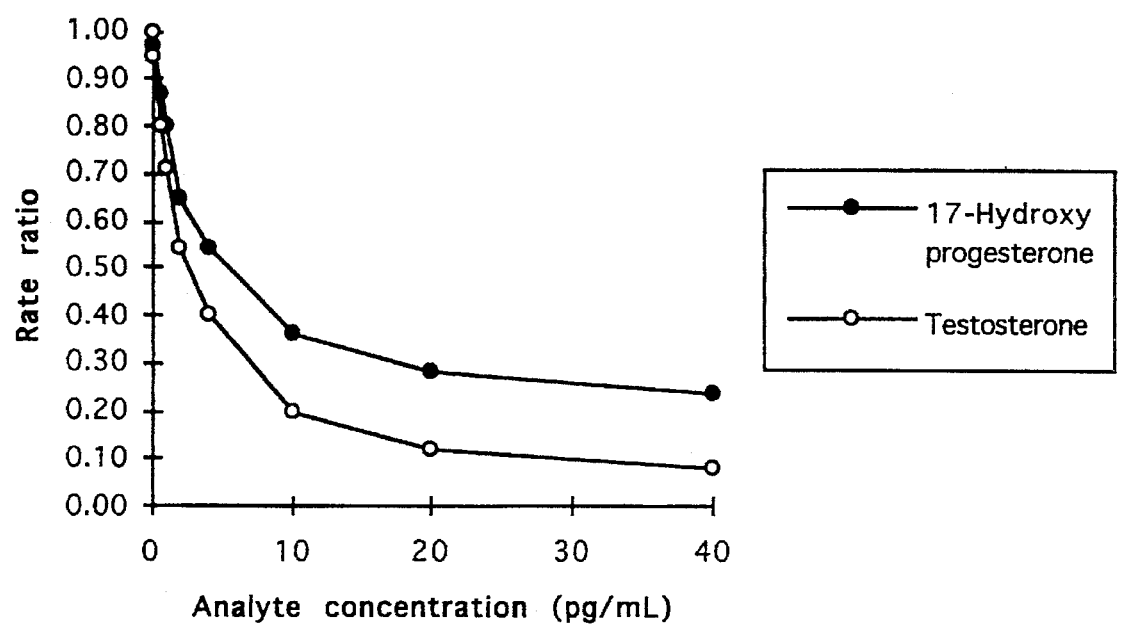
FIG. 6 is a graph illustrating the dose response curves of various steroid-alkaline phosphatase conjugates with anti-progesterone antibody.

Dose Response Curves for Monoclonal Murine 087 Antibodies with Conjugates of Steroid Analogues The dose response curves for anti-progesterone antibody/conjugate combinations were assessed over the range of 0–40 ng/mL (progesterone calibrators A through F). FIG. 6 illustrates the different dose response curves observed for the anti-progesterone murine monoclonal antibody 087 from BiosPacific and conjugates of the steroid analogues 17α-hydroxy progesterone (17αP) and testosterone (T2). For this antibody, a significant improvement in dose response curve was observed with the testosterone conjugate relative to the more structurally similar progesterone analogue 17α-hydroxy progesterone. Calibrators A through F for the progesterone assays were as follows: Calibrator A=0 ng/mL progesterone; Calibrator B=1.0 ng/mL progesterone; Calibrator C=4.0 ng/mL progesterone; Calibrator D=10 ng/mL progesterone; Calibrator E=20 ng/mL progesterone, and Calibrator F=40 ng/mL progesterone.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the amount of estradiol in a test sample comprising the steps of:

a. incubating a mixture of a test sample suspected of containing estradiol, a solid phase coupled to an antibody specific for estradiol, and a conjugate of an estradiol analogue to form estradiol/antibody complexes and conjugate/antibody complexes on said solid phase;

b. separating said solid phase from said mixture;

c. measuring the amount of label present in said mixture or in said solid phase; and d. determining the amount of estradiol in said sample from the amount of label, wherein said conjugate of said estradiol analogue has the formula:

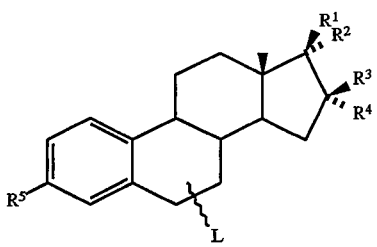

Formula 1a where $R^1$ represents a member selected from the group consisting of OH, H, an alkyl group, an alkenyl group, an alkynyl group, and an alkoxy group;

$R^2$ represents a member selected from the group consisting of OH, H, an alkyl group, an alkenyl group, an alkynyl group, and an alkoxy group;

$R^3$ represents a member selected from the group consisting of OH, H, an alkyl group, an alkenyl group, and an alkynyl group, and an alkoxy group;

$R^4$ represents a member selected from the group consisting of OH, H, an alkyl group, an alkenyl group, and an alkynyl group, and an alkoxy group;

$R^5$ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said estradiol analogue has the formula:

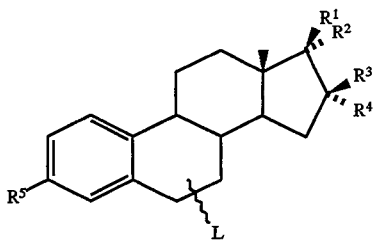

Formula 1a

2. The method of claim 1, wherein said label is selected from the group consisting of catalysts, fluorescent compounds, chemiluminescent compounds, and enzymes.

3. A method for determining the amount of estradiol in a test sample comprising the steps of:

a. incubating a mixture of a test sample suspected of containing estradiol, a solid phase coupled to an antibody specific for estradiol, and a conjugate of an estradiol analogue to form estradiol/antibody complexes and conjugate/antibody complexes on said solid phase;

b. separating said solid phase from said mixture;

c. measuring the amount of label present in said mixture or in said solid phase; and d. determining the amount of estradiol in said sample from the amount of label, wherein said conjugate of said estradiol analogue has the formula:

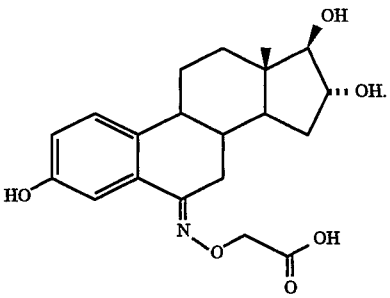

where $R^1$ represents a member selected from the group consisting of OH, H, an alkyl group, an alkenyl group, an alkynyl group, and an alkoxy group;

$R^2$ represents a member selected from the group consisting of OH, H, an alkyl group, an alkenyl group, an alkynyl group; and an alkoxy group;

$R^3$ represents a member selected from the group consisting of OH, H, an alkyl group, an alkenyl group, and an alkynyl group, and an alkoxy group;

$R^4$ represents a member selected from the group consisting of OH, H, an alkyl group, an alkenyl group, an alkynyl group, and an alkoxy group;

$R^5$ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said estradiol analogue has the formula:

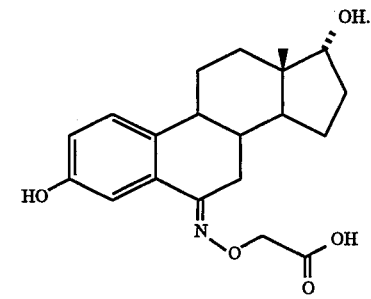

4. The method of claim 3, wherein said label is selected from the group consisting of catalysts, fluorescent compounds, chemiluminescent compounds, and enzymes.

5. A method for determining the amount of estradiol in a test sample comprising the steps of:

a. incubating a mixture of a test sample suspected of containing estradiol, a solid phase coupled to an antibody specific for estradiol, and a conjugate of an estradiol analogue to form estradiol/antibody complexes and conjugate/antibody complexes on said solid phase;

b. separating said solid phase from said mixture;

c. measuring the amount of label present in said mixture or in said solid phase; and d. determining the amount of estradiol in said sample from the amount of label, wherein said conjugate of said estradiol analogue has the formula:

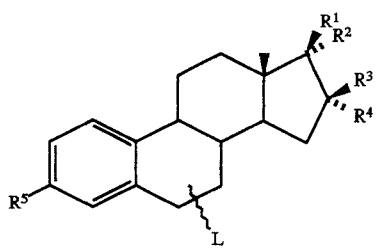

Formula 1a where R¹ represents a member selected from the group consisting of OH, H, an alkyl group, an alkenyl group, an alkynyl group, and an alkoxy group;

R² represents a member selected from the group consisting of OH, H, an alkyl group, an alkenyl group, an alkynyl group, and an alkoxy group;

R³ represents a member selected from the group consisting of OH, H, an alkyl group, an alkenyl group, and an alkynyl group, and an alkoxy group;

R⁴ represents a member selected from the group consisting of OH, H, an alkyl group, an alkenyl group, an alkynyl group, and an alkoxy group;

R⁵ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said estradiol analogue has the formula:

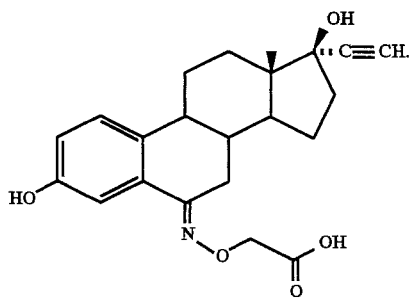

6. The method of claim 5, wherein said label is selected from the group consisting of catalysts, fluorescent compounds, chemiluminescent compounds, and enzymes.

7. A kit for performing a competitive immunoassay for estradiol comprising:

a solid phase coupled to an antibody specific for estradiol, and a conjugate of an estradiol analogue, wherein said conjugate of said estradiol analogue has the formula:

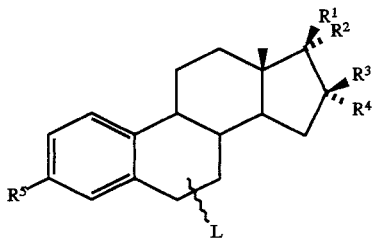

Formula 1a where R¹ represents a member selected from the group consisting of OH, H, an alkyl group, an alkenyl group, an alkynyl group, and an alkoxy group;

R² represents a member selected from the group consisting of OH, H, an alkyl group, an alkenyl group, an alkynyl group, and an alkoxy group;

R³ represents a member selected from the group consisting of OH, H, an alkyl group, an alkenyl group, an alkynyl group, and an alkoxy group;

R⁴ represents a member selected from the group consisting of OH, H, an alkyl group, an alkenyl group, an alkynyl group, and an alkoxy group;

R⁵ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said estradiol analogue has the formula:

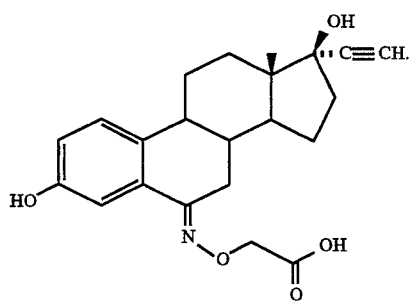

8. The kit of claim 1, wherein said label is selected from the group consisting of catalysts, fluorescent compounds, chemiluminescent compounds, and enzymes.

9. A kit for performing a competitive immunoassay for estradiol comprising:

a solid phase coupled to an antibody specific for estradiol, and a conjugate of an estradiol analogue, wherein said conjugate of said estradiol analogue has the formula:

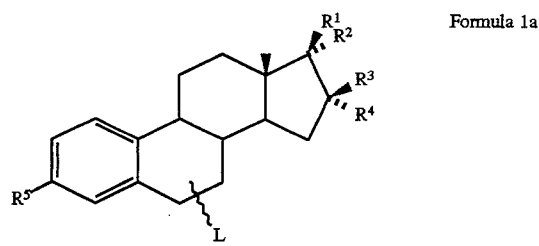

Formula 1a where R¹ represents a member selected from the group consisting of OH, H, an alkyl group, an alkenyl group, an alkynyl group, and an alkoxy group;

R² represents a member selected from the group consisting of OH, H, an alkyl group, an alkenyl group, an alkynyl group, and an alkoxy group;

R³ represents a member selected from the group consisting of OH, H, an alkyl group, an alkenyl group, an alkynyl group, and an alkoxy group;

R⁴ represents a member selected from the group consisting of OH, H, an alkyl group, an alkenyl group, an alkynyl group, and an alkoxy group;

R⁵ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom,, wherein said estradiol analogue has the formula:

27

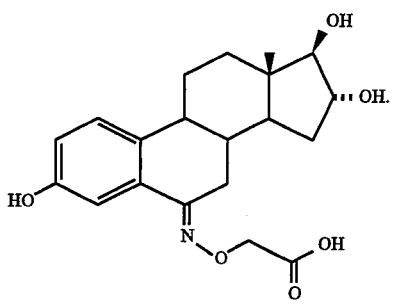

10. The kit of claim 9, wherein said label is selected from the group consisting of catalysts, fluorescent compounds, chemiluminescent compounds, and enzymes.

11. A kit for performing a competitive immunoassay for estradiol comprising:

a solid phase coupled to an antibody specific for estradiol, and a conjugate of an estradiol analogue, wherein said conjugate of said estradiol analogue has the formula:

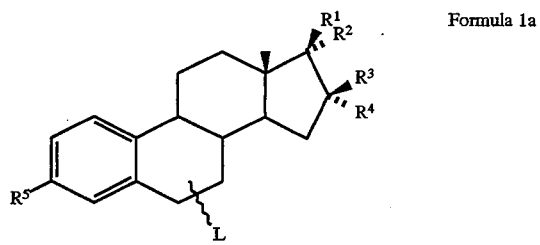

Formula 1a where $R^1$ represents a member selected from the group consisting of OH, H, an alkyl group, an alkenyl group, an alkynyl group, and an alkoxy group;

$R^2$ represents a member selected from the group consisting of OH; H, an alkyl group, an alkenyl group, an alkynyl group, and an alkoxy group;

$R^3$ represents a member selected from the group consisting of OH, H, an alkyl group, an alkenyl group, an alkynyl group, and an alkoxy group;

$R^4$ represents a member selected from the group consisting of OH, H, an alkyl group, an alkenyl group, an alkynyl group, and an alkoxy group;

$R^5$ represents an alkoxy group, or OH;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said estradiol analogue has the formula:

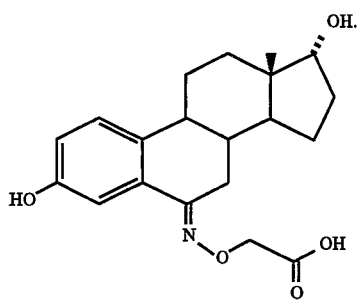

12. The kit of claim 11, wherein said label is selected from the group consisting of catalysts, fluorescent compounds, chemiluminescent compounds, and enzymes.

28

13. A method for determining the amount of progesterone in a test sample comprising the steps of:

a. incubating a mixture of a test sample suspected of containing progesterone, a solid phase coupled to an antibody specific for progesterone, and a conjugate of an progesterone analogue to form progesterone/antibody complexes and conjugate/antibody complexes on said solid phase;

b. separating said solid phase from said mixture;

c. measuring the amount of label present in said mixture or in said solid phase; and d. determining the amount of progesterone in said sample from the amount of label, wherein said conjugate of said progesterone analogue has formula:

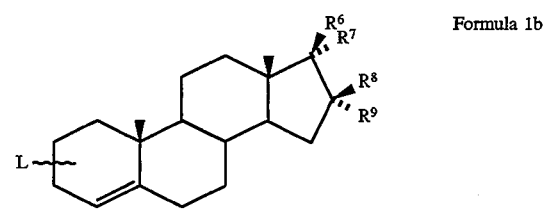

Formula 1b where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group; and an alkoxy group;

$R^9$ represents a member selected from the group consisting of OH, H, an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

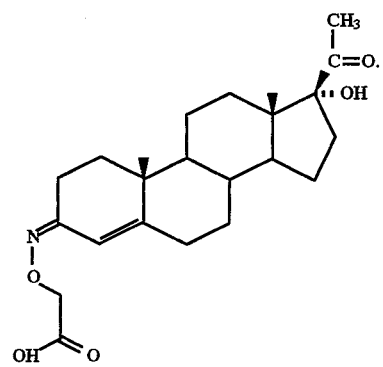

14. The method of claim 13, wherein said label is selected from the group consisting of catalysts, fluorescent compounds, chemiluminescent compounds, and enzymes.

15. A method for determining the amount of progesterone in a test sample comprising the steps of:

a. incubating a mixture of a test sample suspected of containing progesterone, a solid phase coupled to an antibody specific for progesterone, and a conjugate of an progesterone analogue to form progesterone/antibody complexes and conjugate/antibody complexes on said solid phase;

b. separating said solid phase from said mixture;

c. measuring the amount of label present in said mixture or in said solid phase; and d. determining the amount of progesterone in said sample from the amount of label, wherein said conjugate of said progesterone analogue has formula:

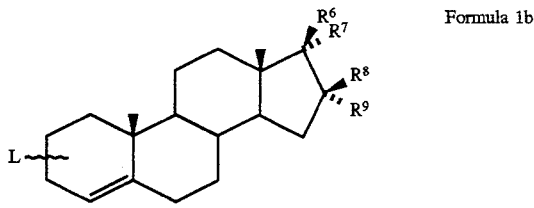

Formula 1b where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group, and an alkoxy group;

$R^9$ represents a member selected from the group consisting of OH, H, an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

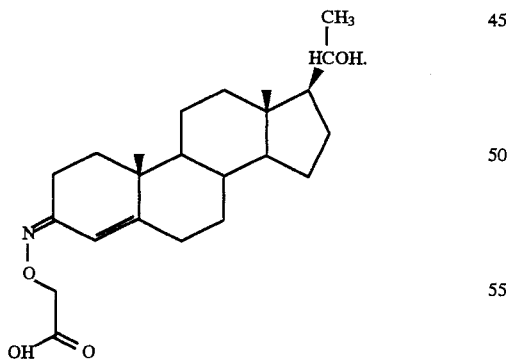

16. The method of claim 15, wherein said label is selected from the group consisting of catalysts, fluorescent compounds, chemiluminescent compounds, and enzymes.

17. A method for determining the amount of progesterone in a test sample comprising the steps of:

a. incubating a mixture of a test sample suspected of containing progesterone, a solid phase coupled to an antibody specific for progesterone, and a conjugate of an progesterone analogue to form progesterone/antibody complexes and conjugate/antibody complexes on said solid phase;

b. separating said solid phase from said mixture;

c. measuring the amount of label present in said mixture or in said solid phase; and d. determining the amount of progesterone in said sample from the amount of label, wherein said conjugate of said progesterone analogue has formula:

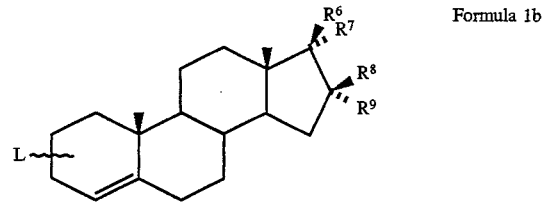

Formula 1b where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group, and an alkoxy group;

$R^9$ represents a member selected from the group consisting of OH, H, an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

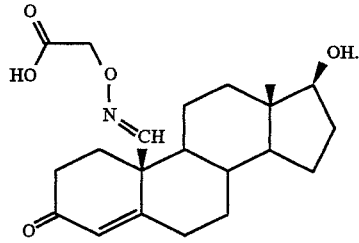

18. The method of claim 17, wherein said label is selected from the group consisting of catalysts, fluorescent compounds, chemiluminescent compounds, and enzymes.

19. A kit for performing a competitive immunoassay for progesterone comprising:

a solid phase coupled to an antibody specific for progesterone, and a conjugate of a progesterone analogue, wherein said conjugate of said progesterone analogue has formula:

Formula 1b

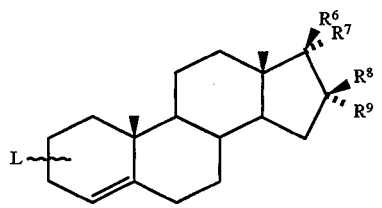

where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group, and an alkoxy group;

$R^9$ represents a member selected from the group consisting of OH, H, an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

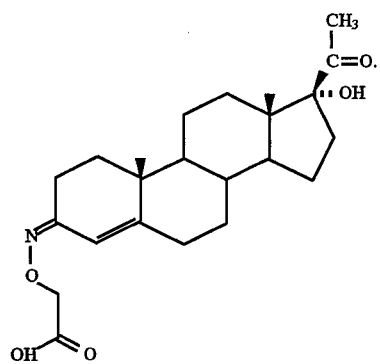

20. The kit of claim 19, wherein said label is selected from the group consisting of catalysts, fluorescent compounds, chemiluminescent compounds, and enzymes.

21. A kit for performing a competitive immunoassay for progesterone comprising:

a solid phase coupled to an antibody specific for progesterone, and a conjugate of a progesterone analogue, wherein said conjugate of said progesterone analogue has formula:

Formula 1b

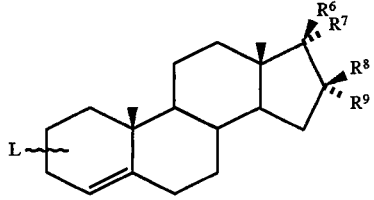

where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group, and an alkoxy group;

$R^9$ represents a member selected from the group consisting of OH, H,. an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

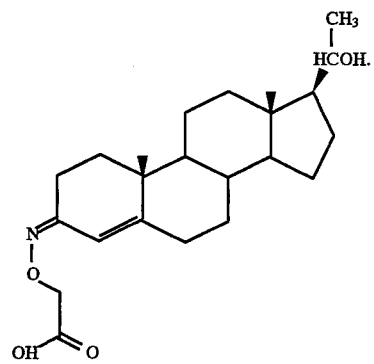

22. The kit of claim 21, wherein said label is selected from the group consisting of catalysts, fluorescent compounds, chemiluminescent compounds, and enzymes.

23. A kit for performing a competitive immunoassay for progesterone comprising:

a solid phase coupled to an antibody specific for progesterone, and a conjugate of a progesterone analogue, wherein said conjugate of said progesterone analogue has formula:

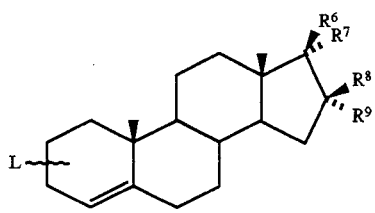

Formula 1b where $R^6$ represents a member selected from the group consisting of OH, H, an alkyl group, an alkenyl group, an alkynyl group, and an alkoxy group;

$R^7$ represents a member selected from the group consisting of OH, H, an alkyl group, an alkenyl group, an alkynyl group, and an alkoxy group;

$R^8$ represents a member selected from the group consisting of OH, H, an alkyl group, an alkenyl group, an alkynyl group, and an alkoxy group;

$R^9$ represents a member selected from the group consisting of OH, H, an alkyl group, an alkenyl group, an alkynyl group, and an alkoxy group;

L represents a label group; provided that the carbon atom at position 16 does not contain two substituents that are attached to the carbon atom at position 16 by an oxygen atom, and further provided that the carbon atom at position 17 does not contain two substituents that are attached to the carbon atom at position 17 by an oxygen atom, wherein said progesterone analogue has the formula:

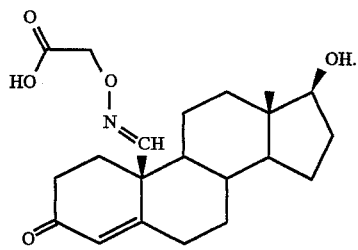

24. The kit of claim 23, wherein said label is selected from the group consisting of catalysts, fluorescent compounds, chemiluminescent compounds, and enzymes.

* * * * *

UNITED STATES PATENT AND TRADEMARK OFFICE
CERTIFICATE OF CORRECTION

Page 1 of 2

PATENT NO. : 5,663,054
DATED : September 2, 1997
INVENTOR(S) : Gregg T. Williams, et. al.

It is certified that error appears in the above-identified patent and that said Letters Patent is hereby corrected as shown below:

Col. 23, line 36 replace "

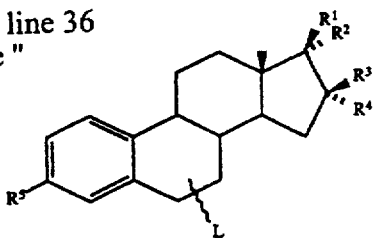

Formula Ia

"

with --

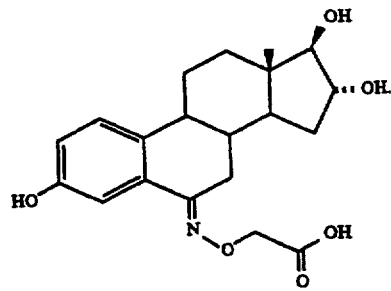

--.

UNITED STATES PATENT AND TRADEMARK OFFICE
CERTIFICATE OF CORRECTION

PATENT NO. : 5,663,054
DATED : September 2, 1997
INVENTOR(S) : Gregg T. Williams, et. al.

It is certified that error appears in the above-identified patent and that said Letters Patent is hereby corrected as shown below:

Col. 24, line 1 replace "

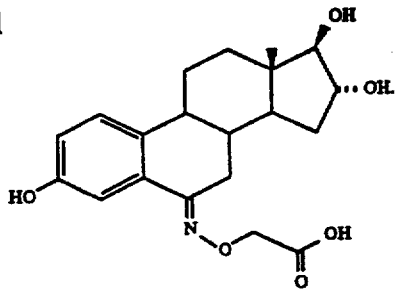

"

with --

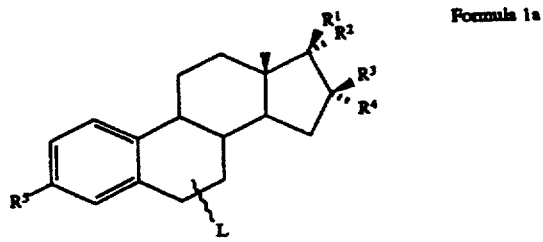

Formula 1a

--.

Signed and Sealed this

Twenty-second Day of September, 1998

Attest:

BRUCE LEHMAN

Attesting Officer

Commissioner of Patents and Trademarks